(12) United States Patent
Bulkes et al.

(10) Patent No.: US 8,463,407 B2
(45) Date of Patent: Jun. 11, 2013

(54) MRI COMPATIBLE IMPLANTED LEAD-ELECTRODE INTERFACE

(75) Inventors: Cherik Bulkes, Sussex, WI (US); Stephen Denker, Mequon, WI (US)

(73) Assignee: Kenergy, Inc., Mequon, WI (US)

( * ) Notice: Subject to any disclaimer, the term of this patent is extended or adjusted under 35 U.S.C. 154(b) by 578 days.

(21) Appl. No.: 12/729,283

(22) Filed: Mar. 23, 2010

(65) Prior Publication Data

US 2010/0249892 A1    Sep. 30, 2010

Related U.S. Application Data

(60) Provisional application No. 61/163,600, filed on Mar. 26, 2009.

(51) Int. Cl.
*A61N 1/18* (2006.01)

(52) U.S. Cl.
USPC .............................. 607/148; 607/154; 600/13

(58) Field of Classification Search
USPC .................... 607/148, 154; 600/13
See application file for complete search history.

(56) References Cited

U.S. PATENT DOCUMENTS

| | | | |
|---|---|---|---|
| 2,966,640 A | 12/1960 | Eiland, Jr. | |
| 5,217,010 A | 6/1993 | Tsitlik et al. | |
| 5,676,694 A | 10/1997 | Boser et al. | |
| 5,861,019 A | 1/1999 | Sun et al. | |
| 6,009,350 A | 12/1999 | Renken | |
| 6,324,431 B1 | 11/2001 | Zarinetchi et al. | |
| 6,459,937 B1 | 10/2002 | Morgan et al. | |
| 6,713,671 B1 | 3/2004 | Wang | |
| 6,738,674 B2 * | 5/2004 | Osypka | 607/122 |
| 6,930,242 B1 | 8/2005 | Helfer | |
| 7,238,883 B2 * | 7/2007 | Zarembo | 174/69 |
| 7,363,090 B2 | 4/2008 | Halperin et al. | |
| 7,917,213 B2 | 3/2011 | Bulkes et al. | |
| 2002/0123776 A1 | 9/2002 | Von Arx et al. | |
| 2003/0036776 A1 | 2/2003 | Foster et al. | |

(Continued)

FOREIGN PATENT DOCUMENTS

| | | |
|---|---|---|
| EP | 1704893 A1 | 9/2006 |
| WO | 2005110540 A1 | 11/2005 |
| WO | 2006023700 A | 3/2006 |
| WO | 2006093685 A | 9/2006 |
| WO | 2006105066 A | 10/2006 |

OTHER PUBLICATIONS

PCT International Search Report.

(Continued)

*Primary Examiner* — Christopher D Koharski
*Assistant Examiner* — Natasha Patel
(74) *Attorney, Agent, or Firm* — Quarles & Brady LLP; George E. Haas

(57) ABSTRACT

An electrical lead for implantation into an animal includes a cable to which a stimulation electrode is connected. The cable has a helical electrical conductor enclosed within an insulating sheath. The stimulation electrode has a tubular first contact band with a threaded lumen into which a portion of the helical electrical conductor is screwed. A second contact band has a threaded aperture and a helical electrode coil is screwed into both the threaded lumen and the threaded aperture. The two contact bands are separated so as to expose a portion of the electrode coil to enable electrical stimulation of tissue of the animal. Particular configurations of the helical electrode coil and the helical electrical conductor render the electrical lead compatible with MRI scanning.

18 Claims, 1 Drawing Sheet

U.S. PATENT DOCUMENTS

| | | |
|---|---|---|
| 2003/0050557 A1 | 3/2003 | Susil et al. |
| 2003/0144721 A1 | 7/2003 | Villaseca et al. |
| 2004/0230271 A1 | 11/2004 | Wang et al. |
| 2005/0102010 A1 | 5/2005 | Lau et al. |
| 2006/0212096 A1 | 9/2006 | Stevenson |
| 2006/0217792 A1 | 9/2006 | Hussein et al. |
| 2006/0247684 A1 | 11/2006 | Halperin et al. |
| 2007/0112398 A1* | 5/2007 | Stevenson et al. .............. 607/63 |
| 2008/0033500 A1 | 2/2008 | Strother et al. |
| 2008/0243218 A1 | 10/2008 | Bottomley et al. |
| 2009/0281592 A1 | 11/2009 | Vase |

OTHER PUBLICATIONS

Environmental Chemistry.com list of Periodic Table of Elements as sorted by Electrical Conductivity, accessed Dec. 4, 2009. http://environmentalchemistry.com/yogi/periodic/electrical.html.

Properties of Nitinol webpage, accessed Dec. 4, 2009. http://www.peiertech.com/Literature/Properties%20of%20Nitinol.pdf.

* cited by examiner

MRI COMPATIBLE IMPLANTED LEAD-ELECTRODE INTERFACE

CROSS-REFERENCE TO RELATED APPLICATIONS

This application claims benefit of U.S. Provisional Patent Application No. 61/163,600 filed Mar. 26, 2009.

STATEMENT REGARDING FEDERALLY SPONSORED RESEARCH OR DEVELOPMENT

Not Applicable

BACKGROUND OF THE INVENTION

1. Field of the Invention

The present invention relates to implantable electronic medical devices, such as cardiac pacemakers and defibrillators for example, for stimulating tissue of animal for the therapeutic purposes; and more particularly to electrical leads for such devices.

2. Description of the Related Art

Numerous medical conditions, such as cardiac and neurological dysfunctions, are treated by an implanted electronic device, which provides electrical stimulation to the affected tissue of the animal. These devices have a plurality of metal components, including the case enclosing electronic circuits and wire leads extending from the case to electrodes in contact with the tissue to be stimulated or monitored.

Magnetic resonance imaging (MRI) is commonly employed to view internal organs of medical patients. To create an image, the patient is placed into very strong static and varying magnetic (gradient) and radio frequency (RF) fields and thus MRI generally is prohibited for patients with implanted ferromagnetic and or electrically conductive objects. Although it is feasible to minimize and even eliminate the use of ferromagnetic materials in implanted apparatus, electronic devices, such as cardiac pacemakers and defibrillators, require electrically conductive components and lead structures that are affected by the fields produced by an MRI scanner.

It has been a long-standing goal to make implanted devices MRI compatible so that this imaging modality can be used with patients having those devices. There are several reasons for achieving this goal. Firstly, incompatible implant components and leads induce susceptibility difference, which destroys DC magnetic field homogeneity of the MRI scanner, thereby negatively affecting the imaging performance. Secondly, the MRI field can produce eddy currents in the implanted conductive materials, which currents generate heat that adversely affects patient and degrade the scanner performance by field distortion. Thirdly, the MRI RF, gradient and magnetic fields may ruin the implanted device. Fourthly, the incompatible implant material can potentially cause serious internal injuries to the patient.

Typical electrical leads used with implanted medical devices had a proximal end connected to the electronic circuit inside the main case of the device and a distal end having an external electrode to contact the tissue of the animal being stimulated. The connection of the conductor in the lead to the external electrode also is important to the proper functioning of the implanted medical device. Good electrical and mechanical connection must be established.

Previously the lead conductor was attached by an adhesive that bonded to one or more grooves in a conductive ring member that served as the electrode.

In other places, a separate connector was used to interconnect two conductors. Here the connector has an electrically conductive body with a first end portion coupled to one conductor and a second end portion coupled to a the other conductor. In one example, electrically conductive connector had one or more internal grooves (or threads) to which the conductor was coupled. Conductors also were secured to the electrically conductive connector by rotary swaging, laser or resistance welding, brazing, mechanical swaging, or crimping. In examples in which one or both of first conductor or second conductor are coupled via one or more external grooves (such as those associated with screw threads), shrink tubing or a compressive/elastic lead body may be used to further secure such conductors to connector.

The conductor of an electrical lead may also be coupled to a ring member using a variety of techniques. One technique includes a securing member disposed around the distal end portion of the conductor and the ring member. Optionally, one or more grooves or threads may be formed on the ring member and the securing member is deformed over the conductor thereby making connection the ring member. In a first technique, portions of the securing member are pushed into or over the one or more grooves or threads. A second technique uses a conductive adhesive to couple the conductor to the ring member. A third coupling technique involves forming one or more grooves or threads on the ring member and urging the conductor onto the one or more grooves or threads. Such urging may come by way of the compressive nature of the lead body or a removable preformed mandrel.

In any case, lead-electrodes come in a variety of configurations including tip and ring for pacing and coiled configuration for implantable cardiac defibrillator (ICD) applications. The electrode structure and lead-electrode interface must be selected to minimize the build up of induced local electrical fields, which can give rise to radio frequency burns and tissue damage. In general, the lead-electrode material choices affect image quality and MRI compatibility. The lead-electrode interface needs to be mechanically fatigue resistant, yet electrically conductive, and bio-compatible.

Therefore, there is a desire to provide an electrode structure and a lead-electrode interface that satisfies the above requirements. In addition, it is desired that the interface has minimal complexity for ease of manufacture.

SUMMARY OF THE INVENTION

The present invention is directed toward an electrical lead for a medical device adapted to be implanted in an animal to electrically stimulate the animal's tissue. In particular the invention addresses interfacing a conductor of the electrical lead with the electrode structure.

The electrical lead includes a cable with a helical electrical conductor enclosed within a sheath of electrical insulating material. A stimulation electrode is provided for applying electric current to tissue of the animal. The stimulation electrode comprises a first contact band that has a tubular shape with a threaded lumen and a second contact band that has a threaded aperture. A helical electrode coil is screwed into both the threaded lumen and the threaded aperture. Preferably the first and second contact bands are separated from each other, thereby exposing a section of the helical electrode coil. That exposed portion and the two contact bands are thereby adapted to contact the tissue of the animal for delivering a stimulus to that tissue or for sensing electrical activity in the animal. A portion of the helical electrical conductor of the cable is screwed into the threaded lumen.

Another aspect of the electrical lead is the helical configuration of the conductors wherein the adjacent turns are spaced apart. This avoiding the presentation of a continuous surface that would otherwise give rise to induction heating when subjected to electromagnetic fields in an MRI scanner. The electrode described here is wound such that the adjacent turns do not touch and have a specific pitch. The physical dimensions, wire size, spacing, diameter, underlying insulation materials are all chosen to present an equivalent resistance, inductance, capacitance (RLC) structure that exhibits a high impedance at the frequencies of the MRI fields.

Unlike prior stimulation leads, the inventive aspect does not need adhesives, welds or urging (force) and avoids the associated compromise in fatigue resistance in lead-electrode interfaces while being MRI compatible.

DETAILED DESCRIPTION OF THE INVENTION

Although the present invention is being described in the context of cardiac pacing and implanting a stimulation electrode in a vein or artery of the heart, the present apparatus can be employed to stimulate other areas and organs of a human body.

Figure 1:
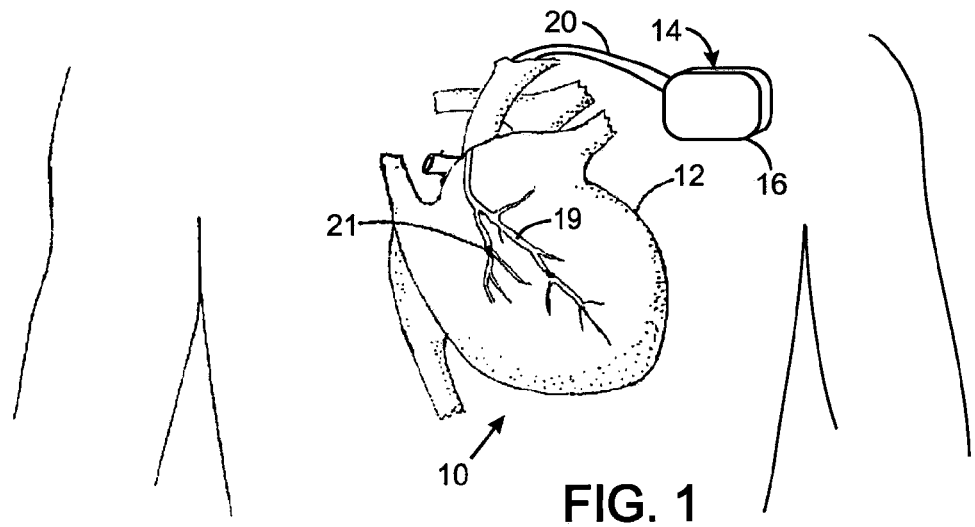
FIG. 1 is a representation of a cardiac pacing system implanted in a medical patient.

With initial reference to FIG. 1, a medical apparatus 10 comprises a stimulator 14, such as a cardiac pacing device or implantable cardiac defibrillator (ICD). The stimulator 14 has a housing 16 implanted under the skin of the patient and containing conventional electronic circuitry for detecting when cardiac stimulation is required and producing electrical pulses for stimulating a heart 12 to contract.

The electronic circuitry in the stimulator 14 is connected to one or more electrical leads 20 that enter a vein or artery and extend through the vasculature of the patient to locations in smaller blood vessels 19 at which stimulation of the heart is desired. At such locations 21, the electrical lead 20 is connected to a stimulation electrode 22 (FIG. 2) secured to the blood vessel wall so as to have better transfer efficiency than when if the electrode floats in the blood pool. The stimulation electrode 22 may be placed proximate to the sinus node (e.g., in the coronary sinus vein), the atria, or the ventricles of the heart, for example.

The electrical lead 20 and the stimulation electrode 22 attached thereto have a unique construction that is not only particularly useful for various electrical stimulation applications, but also is compatible with magnetic resonance imaging.

Figure 2:
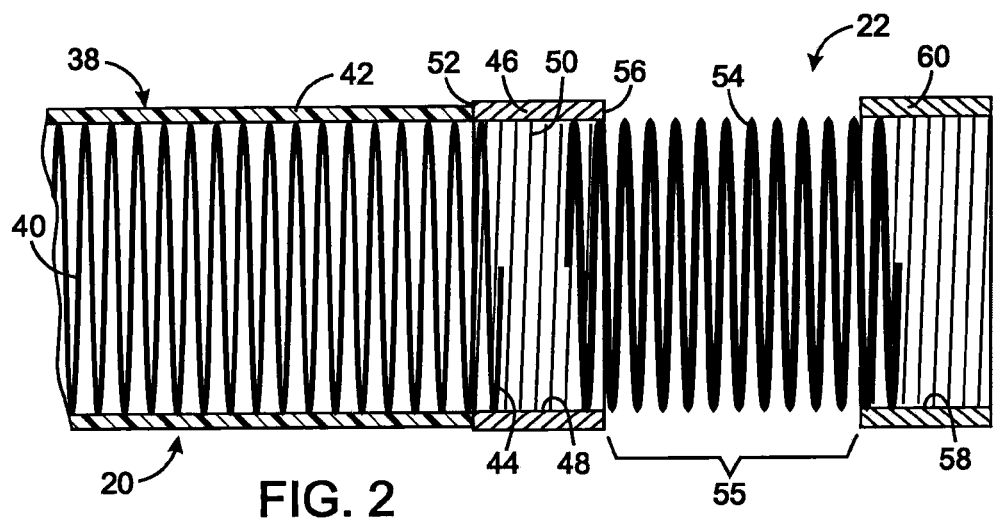
FIG. 2 is an enlarged view of the distal end of the lead-electrode interface according to the present invention.

With reference to FIG. 2, the stimulation electrode 22 is located at the distal end of the electrical lead 20 that is remote from the stimulator 14. The electrical lead 20 has a cable 38 with an internal lead conductor 40 that is coiled in a helix which extends longitudinally within an outer tubular sheath 42. The lead conductor 40 has an exposed end portion 44 projecting beyond the sheath 42. The lead conductor 40 may be made of stainless steel or a nickel-cobalt-chromium-molybdenum alloy. The adjacent turns of the helical lead conductor 40 do not touch each other. The insulating sheath 42 isolates the lead conductor 40 from direct external contact with blood and tissues within the animal. The insulating sheath 42 may be made of urethane that provides not only electrical insulation, but is relatively flexible in order to allow the lead to be guided through the vasculature of the animal.

The stimulation electrode 22 comprises a first contact band 46 that has a tubular shape with a lumen 48 which has a first set of screw threads 50 on the lumen surface. The exposed end portion 44 of the lead conductor 40 is screwed into a first side 52 of the first contact band 46, thereby meshing with the screw threads 50. To accommodate this connection the pitch of the helical lead conductor 40 is identical to the pitch of the screw threads 50. That engagement of the helical lead conductor with the lumen screw threads secures the cable 38 to the first contact band 46 and thus to the stimulation electrode 22. This screw connection provides an electrical and a mechanical coupling between the cable 38 and the stimulation electrode 22.

Alternatively, the cable 38 may have a plurality of helically coiled conductors interleaved in a spiraling manner along its length. With this configuration each conductor is screwed into the interior lumen 48 of the first contact band 46.

The stimulation electrode 22 further includes an electrode coil 54, comprising an uninsulated electrically conductive wire that is formed in a helix. The electrode coil 54 is a biocompatible, non-magnetic material, such as a platinum-iridium alloy or an equivalent. One end of the helical electrode coil 54 is screwed into the threaded lumen 48 at a second side 56 of the first contact band 46. This secure connection provides both a mechanical and an electrical coupling of the electrode coil to the first contact band. The opposite end of the helical electrode coil 54 is screwed into a threaded aperture 58 in a second contact band 60. Although it is preferred that the threaded aperture 58 extend entirely through the second contact band 60, that aperture may not open through the other side of the second contact band. As shown in the drawings, the spiral turns of the electrode coil 54 engage the screw threads on the interior surface of the aperture 58 in the second contact band 60. To accommodate this connection the helical electrode coil 54 and the screw threads in the first and second contact band 46 and 60 all have the same pitch. By screwing the helical lead conductor 40 and the helical electrode coil 54 into the respective first and second contact bands 46 and 60, electrical and mechanical connection of those components is achieved without the use of any welding, brazing, adhesives, swaging, or crimping. The first and second contact bands 46 and 60 are separated from each other thereby exposing a section 55 of the helical electrode coil to bodily tissue when the lead in implanted in an animal.

Both the first and second contact bands 46 and 60 are made of biocompatible material, such as a platinum-iridium alloy or an equivalent.

In one embodiment, the stimulation electrode 22 is relatively short, e.g., 1 to 3 mm, and the two contact bands 46 and 60 and the electrode coil 54 combine to form a ring electrode of a conventional "ring and tip" electrode pair used in cardiac pacing. Alternatively, the stimulation electrode 22 can be longer, e.g., 10 to 75 mm, where the electrical lead is part of an implantable cardiac defibrillator. In this latter application, the larger conductive exterior surface area provides a high current density during application of the defibrillation discharge.

Figure 3:
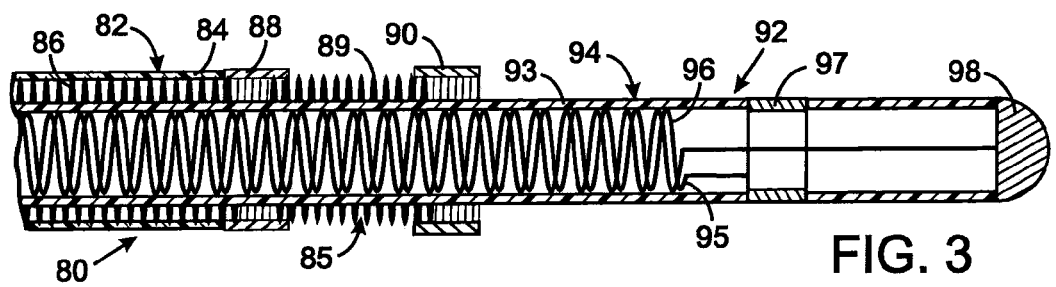
FIG. 3 illustrates another embodiment of the distal end from which a sensing electrode projects.

FIG. 3 depicts another electrical lead 80 according to the present invention that, in addition to having a stimulation electrode 85, has an additional pair of electrodes 97 and 98 at its distal end. Those additional electrodes 97 and 98 can be used for either sensing electrical activity in the patient or for tissue stimulation. For example, the stimulation electrode 85 may be used for defibrillation while the additional electrodes 97 and 98 are used for cardiac pacing.

Specifically, electrical lead 80 has a first cable 82 that extends from the stimulator 14, such as the one shown in FIG. 1. The first cable 82 has an outer sheath 84 of electrical insulating material that surrounds a first lead conductor 86 that is wound in a helix. The first lead conductor 86 engages the first contact band 88 of a stimulation electrode 85. In particular, the helical first lead conductor 86 is screwed into the internal screw threads in the lumen of the first contact band 88. The stimulation electrode 85 also has an uninsulated helical electrode coil 89 which enables that electrode coil to be screwed into the other end of the first contact band 88 and into a threaded lumen in a second contact band 90. Both the first and second contact bands 88 and 90 are made of electrically conductive material. Thus, the screw connections of the first lead conductor 86 and the electrode coil 89 with the two contact bands 88 and 90 provide an electrical and a mechanical connection between those components in a manner similar to that described with respect to the device shown in FIG. 2.

A physically separate second lead 92 comprises a second cable 94 that extends from the stimulator 14 longitudinally through the first cable 82 within the center of the first lead conductor 86. The second cable 94 extends not only through the center of the first cable 82, but also through center bore in the stimulation electrode 85 and outward beyond the second contact band 90. The second cable 94 has a similar spiral or helical pair of insulated conductors 95 and 96 surrounded by an insulating second sheath 93. The second sheath 93 further electrically insulates pair of insulated conductors 95 and 96 from the lead conductor 40 and the stimulation electrode 85 of the first electrical lead 80.

The section of the second cable 94 that projects from the distal end of the first electrical lead 80 has a ring electrode 97 spaced inward from a hemispherical tip electrode 98 at the extreme end. The first insulated conductor 95 is electrically connected to the ring electrode 97 and the second insulated conductor 96 is electrically connected to the tip electrode 98.

For the various embodiments of the present electrical lead, MRI compatibility is achieved by a non-shorted structure of the electrode coil 54 or 89 that has space between adjacent turns, thus avoiding an electrical short between the turns often found in implantable cardiac defibrillator leads. Such spacing avoids the presentation of a continuous surface that would otherwise give rise to induction heating from the very strong electromagnetic fields produced by an MRI scanner. Furthermore, the turns of the electrode coil 54 or 89 have a specific pitch. That pitch combined with coil diameter, wire gauge, and insulation materials are all chosen to provide an equivalent structure that has a resistance, inductance and capacitance that provides a high impedance at MRI frequencies. Typical MRI frequencies are 64 MHz for a 1.5 Tesla scanner and 128 MHz for a 3.0 Tesla scanner. The more turns per unit of length of the lead increases the inductance and capacitance. The high impedance resulting form the pitch of the electrode coil 54 or 89 inhibits electric current from being produced in the stimulation electrode 22 or 85 by the electromagnetic fields of an MRI scanner.

The pitches of the helical lead conductors 40, 86, 95 and 96 also provide a high impedance, of at least 3000 ohms from the associated electrode 22, 85, 97 or 98 to the respective lead's proximal end that is connected to the stimulator 14. Such high impedance significantly attenuates or inhibits formation of radio frequency currents induced in the respective lead 20, 80 or 92 by the MRI fields, while presenting low impedance to direct current of stimulation pulses produced by the stimulator 14.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

The invention claimed is:

1. An electrical lead that is adapted for implantation in an animal, said electrical lead comprising:
   a first cable having a helical electrical conductor enclosed within a sheath of electrical insulating material;
   a stimulation electrode for applying electric current to tissue of an animal, the stimulation electrode includes a first contact band that has a tubular shape with a threaded lumen, a second contact band that has a threaded aperture, and a helical electrode coil that is screwed into both the threaded lumen and the threaded aperture, and wherein a portion of the helical electrical conductor of the first cable is screwed into the threaded lumen.

2. The electrical lead as recited in claim 1 wherein the first and second contact bands are separated from each other thereby exposing a section of the helical electrode coil, wherein the section is adapted to contact tissue of the animal upon implantation.

3. The electrical lead as recited in claim 1 wherein the helical electrode coil has turns that are spaced from each other.

4. The electrical lead as recited in claim 3 wherein spacing between the turns of the helical electrode coil is selected to produce a high impedance at a frequency of an electromagnetic field generated by a magnetic resonance imaging scanner, thereby inhibiting electrical current from being produced in the stimulation electrode by the electromagnetic field.

5. The electrical lead as recited in claim 1 wherein the helical electrical conductor has a pitch that creates an impedance of at least 3000 ohms between a proximal end of the lead and the stimulation electrode.

6. The electrical lead as recited in claim 1 further comprising:
   a second cable extending longitudinally through the first cable and through and beyond the stimulation electrode, the second cable having a helical additional conductor; and
   an additional electrode connected to the helical additional conductor.

7. The electrical lead as recited in claim 6 wherein the additional electrode is ring-shaped.

8. The electrical lead as recited in claim 6 wherein the second cable further comprises an additional sheath of electrically insulating material extending around the helical additional conductor.

9. An electrical lead that is adapted for implantation in an animal, said electrical lead comprising:
   a cable having a helical electrical conductor enclosed within a sheath of electrically insulating material;
   a stimulation electrode for applying electric current to tissue of an animal, the stimulation electrode has first contact band with first and second sides and a threaded lumen extending between the first and second sides, a second contact band that has third and fourth sides and a threaded aperture extending between the third and fourth sides, and a helical electrode coil that is screwed into the threaded lumen from the second side of the first contact band and is screwed into the threaded aperture from the third side of the second contact band, wherein the first and second contact bands are separated from each other thereby exposing a section of the helical electrode coil to an exterior of the electrical lead, and wherein a portion of the helical electrical conductor of the cable is screwed into the threaded lumen from the first side of the first contact band.

10. The electrical lead as recited in claim 9 wherein the helical electrical coil has turns that are spaced from each other.

11. The electrical lead as recited in claim 10 wherein spacing between the turns of the helical electrode coil is selected to produce a high impedance at a frequency of an electromagnetic field generated by a magnetic resonance imaging scanner, thereby inhibiting electrical current from being produced in the stimulation electrode by the electromagnetic field.

12. The electrical lead as recited in claim 9 wherein the helical electrical conductor has a pitch that creates an impedance of at least 3000 ohms between a proximal end of the lead and the stimulation electrode.

13. The electrical lead as recited in claim 9 further comprising:
 a sensing cable extending longitudinally through the cable and the stimulation electrode, the sensing cable having helical sensing conductor; and
 a sensing electrode having a ring shape and connected to the helical sensing conductor.

14. The electrical lead as recited in claim 13 wherein the helical sensing conductor is screwed into a threaded aperture in the sensing electrode.

15. The electrical lead as recited in claim 13 wherein the sensing cable further comprises a sensing sheath of electrically insulating material extending around the helical sensing conductor.

16. The electrical lead as recited in claim 1 wherein each of the first and second contact band is adapted to contact the tissue of the animal.

17. The electrical lead as recited in claim 1 wherein the first contact band is spaced from the second contact band with the helical electrode coil extending there between.

18. The electrical lead as recited in claim 9 wherein each of the first and second contact band is adapted to contact the tissue of the animal.

* * * * *